US010456212B2

(12) United States Patent
Gonzalez-Martinez et al.

(10) Patent No.: US 10,456,212 B2
(45) Date of Patent: Oct. 29, 2019

(54) SYSTEMS AND METHODS FOR SAFE, PRECISE STEREOTACTIC IMPLANTATION

(71) Applicant: THE CLEVELAND CLINIC FOUNDATION, Cleveland, OH (US)

(72) Inventors: Jorge A. Gonzalez-Martinez, Moreland Hills, OH (US); John Gale, Shaker Hts., OH (US); Anthony Shawan, Brecksville, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 609 days.

(21) Appl. No.: 15/142,730

(22) Filed: Apr. 29, 2016

(65) Prior Publication Data
US 2016/0317241 A1 Nov. 3, 2016

Related U.S. Application Data

(60) Provisional application No. 62/209,558, filed on Aug. 25, 2015, provisional application No. 62/154,279, filed on Apr. 29, 2015.

(51) Int. Cl.
*A61B 17/00* (2006.01)
*A61B 90/11* (2016.01)
(Continued)

(52) U.S. Cl.
CPC ............ *A61B 90/11* (2016.02); *A61N 1/0526* (2013.01); *A61B 90/14* (2016.02)

(58) Field of Classification Search
CPC ......... A61B 90/10; A61B 90/11; A61B 90/14; A61B 2090/101; A61B 2090/103
(Continued)

(56) References Cited

U.S. PATENT DOCUMENTS 4,805,615 A 2/1989 Carol
6,132,437 A 10/2000 Omurtag et al.
(Continued)

FOREIGN PATENT DOCUMENTS

WO 2007059452 A2 5/2007
WO 2009124244 A1 10/2009

OTHER PUBLICATIONS

Antony, Arun R., et al. "Functional connectivity estimated from intracranial EEG predicts surgical outcome in intractable temporal lobe epilepsy." PloS one 8.10 (2013): e77916.
(Continued)

*Primary Examiner* — Melanie R Tyson
(74) *Attorney, Agent, or Firm* — Tarolli, Sundheim, Covell & Tummino LLP

(57) ABSTRACT

The present disclosure relates generally to precise stereotactic implantation of an instrument (e.g., a recording electrode, a stimulating electrode, a biopsy instrument, a catheter, a delivery device, and the like) into a target area in a patient's brain. As such, one aspect of the present disclosure can relate to a stereotactic device that can be used to accomplish the precise implantation of the instrument. The stereotactic device can include a body to secure the stereotactic device to the patient's head. In some instances, the body can have a u-shape. The stereotactic device can also include a guide attached between sides of the body to move an instrument holder into place above a target area. The guide can be locked in position to lock the instrument holder in the place to facilitate injection of the instrument into the target area.

5 Claims, 8 Drawing Sheets

(51) Int. Cl.
*A61N 1/05* (2006.01)
*A61B 90/14* (2016.01)

(58) Field of Classification Search
USPC .......................................................... 606/130
See application file for complete search history.

(56) References Cited

U.S. PATENT DOCUMENTS

| | | | |
|---|---|---|---|
| 6,319,189 B1* | 11/2001 | Halpern ............... | A61N 5/1027 600/3 |
| 7,925,328 B2 | 4/2011 | Urquhart et al. | |
| 2004/0167542 A1 | 8/2004 | Solar et al. | |
| 2005/0165299 A1 | 7/2005 | Kressy et al. | |
| 2009/0112084 A1* | 4/2009 | Piferi .................... | G01R 33/286 600/421 |
| 2010/0030184 A1* | 2/2010 | Boulis ................ | A61B 17/0206 604/500 |
| 2011/0040304 A1 | 2/2011 | Li et al. | |
| 2012/0203236 A1* | 8/2012 | Mamourian ....... | A61B 17/3403 606/96 |

OTHER PUBLICATIONS

Rei Enatsu, et al. "Combining stereo-electroencephalography and subdural electrodes in the diagnosis and treatment of medically intractable epilepsy." Journal of Clinical Neuroscience 21.8 (2014): 1441-1445.

Enatsu, Rei, et al. "Posterior cingulate epilepsy: clinical and neurophysiological analysis." Journal of Neurology, Neurosurgery & Psychiatry (2013): jnnp-2013.

Gonzalez-Martinez, Jorge et al. "Stereotactic placement of depth electrodes in medically intractable epilepsy: Technical note." Journal of neurosurgery 120.3 (2014): 639-644.

Gonzalez-Martinez, Jorge, et al. "Stereoelectroencephalography in the "difficult to localize" refractory focal epilepsy: early experience from a North American epilepsy center." Epilepsia 54.2 (2013): 323-330.

Gonzalez-Martinez, Jorge, and Deepak Lachhwani. "Stereoelectroencephalography in children with cortical dysplasia: technique and results." Child's Nervous System 30.11 (2014): 1853-1857.

Gonzalez-Martinez, Jorge and Imad M. Najm. "Indications and selection criteria for invasive monitoring in children with cortical dysplasia." Child's Nervous System 30.11 (2014): 1823-1829.

Gonzalez-Martinez, Jorge, et al. "Stereoelectroencephalography in children and adolescents with difficult-to localize refractory focal epilepsy." Neurosurgery 75.3 (2014): 258-268.

Serletis, Demitre, et al. "The stereotactic approach for mapping epileptic networks: a prospective study of 200 patients: Clinical article." Journal of neurosurgery 121.5 (2014): 1239-1246.

Vadera, Sumeet, Richard Burgess, and Jorge Gonzalez-Martinez. "Concomitant use of stereoelectroencephalography (SEEG) and magnetoencephalographic (MEG) in the surgical treatment of refractory focal epilepsy." Clinical neurology and neurosurgery 122 (2014): 9-11.

PCT International Search and Written Opinion for PCT/US2016/030151, dated Jul. 22, 2016, pp. 1-15.

\* cited by examiner

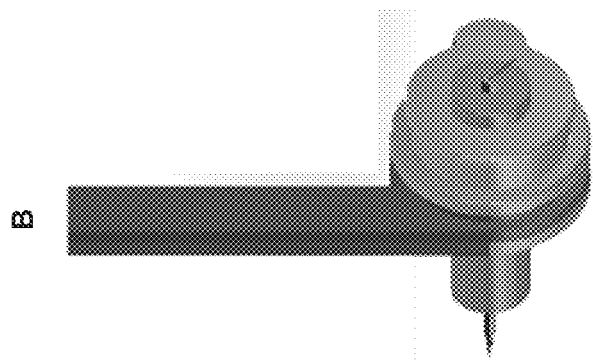
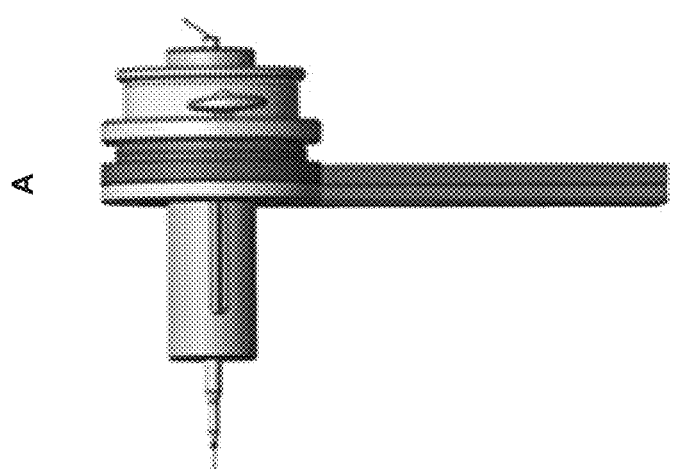
FIG. 8

SYSTEMS AND METHODS FOR SAFE, PRECISE STEREOTACTIC IMPLANTATION

CROSS-REFERENCE TO RELATED APPLICATIONS

This application claims the benefit of U.S. Provisional Application No. 62/209,558, filed Aug. 25, 2015, entitled SYSTEMS AND METHODS FOR SAFE, PRECISE STEREOTACTIC IMPLANTATION, which is incorporated herein by reference in its entirety. This application also claims the benefit of U.S. Provisional Patent Application No. 62/154,279, filed Apr. 29, 2015, entitled SYSTEMS AND METHODS FOR SAFE, PRECISE STEREOTACTIC IMPLANTATION, which is incorporated herein by reference in its entirety.

TECHNICAL FIELD

The present disclosure relates generally to stereotactic surgery and, more specifically, to systems and methods can employ a stereotactic device for safe, precise stereotactic implantation of the medical instrument into the target area of the patient's body.

BACKGROUND

Epilepsy is among the most common disorders of the nervous system, affecting 1-2% of the world's population. A portion of the patients diagnosed with epilepsy have "medically intractable" epilepsy, in which seizures do not respond to antiepileptic drugs. In many cases, medically intractable epilepsy is sufficiently debilitating to warrant the risks of surgery. Stereo-electroencephalography (SEEG) can be used for surgical planning to evaluate the intractable epilepsy. With SEEG, the seizure onset zone and areas of spiking can be identified by electrodes in different areas within and around epileptic lesions and areas suspected to be part of the seizure network. The electrodes can be implanted in the different areas using a traditional stereotactic frame, such as the Talairach frame, the Leksell frame, and the CRW frame. However, these traditional stereotactic frames are cumbersome and require multiple coordinate adjustments, which lead to breaks in sterility. Alternatively, a stereotactic robotic device can offer advantages to traditional stereotactic frames with regard to safety and reliability, but at a higher cost.

SUMMARY

The present disclosure relates generally to stereotactic surgery. The stereotactic surgery of the present disclosure can be performed with a stereotactic device that provides the safety and reliability of the robotic device at the lower cost of the traditional stereotactic devices. Accordingly, the present disclosure relates, more specifically, to systems and methods that can employ the stereotactic device for safe, precise stereotactic implantation of a medical instrument within a target area of a patient's body. For example, the medical instrument can be a recording electrode, a stimulating electrode, a biopsy instrument, a catheter, a drug delivery device, or the like.

In one aspect, the present disclosure includes a stereotactic device that can be used to accomplish the precise implantation of a medical instrument (e.g., a recording electrode, a stimulating electrode, a biopsy instrument, a catheter, a delivery device, and the like) in a target area of a patient's body. Indeed, the stereotactic device can be used to implant a plurality of instruments into a plurality of target areas within the patient's brain using a single coordinate system. The stereotactic device can include a body that includes at least two sides separated by a distance greater than a width of a patient's head. In some instances, the body can have a u-shape to fit around the patient's head. The stereotactic device can also include a guide extending between two sides of the body, moveable along the length of the two sides of the body, and lockable above a target area within the patient's head. The stereotactic device can also include an instrument holder attached to the guide to receive the medical instrument for injection into the target area within the patient's head.

In another aspect, the present disclosure includes a method for implanting medical instruments into target areas in a patient's head. The method can include fixing a stereotactic device to a frame attached to the patient's head. The stereotactic device includes a body comprising at least two sides separated by a distance greater than a width of a patient's head; and a guide extending between two sides of the body. After fixing the stereotactic device, the guide can be moved to a location above a target area within the patient's head and the guide can be locked at the location. A medical instrument can be implanted to the target area within the patient's head through the guide. After the implantation, the guide can be unlocked and moved to a second location above a second target area within the patient's head. The guide can be locked at the second location, and a second medical instrument can be implanted to the second target area within the patient's head through the guide.

In a further aspect, the present disclosure includes a system that can be used to implant a plurality of instruments into a plurality of target areas within a patient's brain using a single coordinate system. The system can include a frame to attach to the patient's head. The system can also include a body to interface with the frame. For example, the body can be locked into a position against the frame. The body can include at least two sides separated by a distance greater than a width of the patient's head. For example, the body can be u-shaped. The system can also include a guide extending between two sides of the body. The guide can moveable along the length of the two sides of the body, and lockable above a target area within the patient's head to facilitate implantation of an instrument into the target area within the patient's head. The guide is moveable and lockable above a plurality of different target areas within the patient's head to facilitate the implantation of a plurality of instruments into a plurality of different target areas within the patient's head using a single coordinate system.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 8 shows different views of an example of a bulls-eye lateral implantation system (BLIS) that can be used with a stereotactic device.

DETAILED DESCRIPTION

I. Definitions

Figure 1:
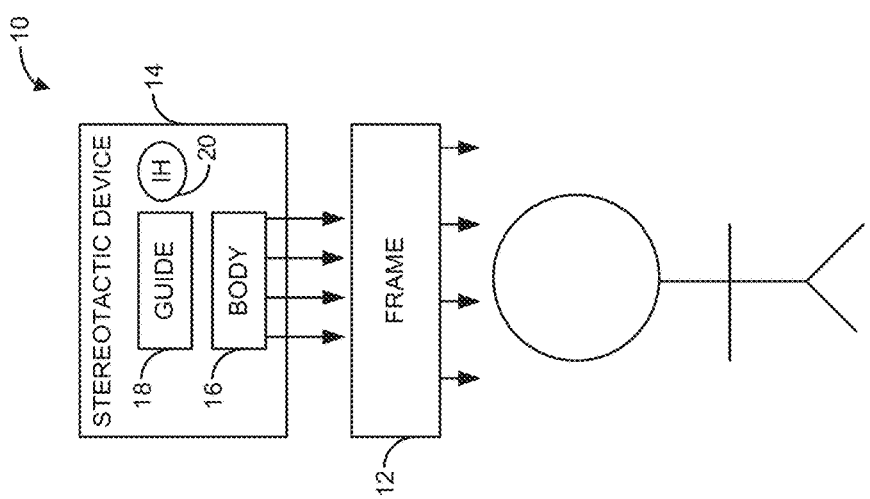
FIG. 1 is a diagram of a stereotactic implantation system in accordance with an aspect of the present invention.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "stereotactic" and "stereotaxic" can refer to a technique for locating one or more points inside a patient's body (e.g., the brain) using an external, three-dimensional frame of reference based on a three-dimensional coordinate system.

As used herein, the term "three dimensional coordinate system" can refer to a three-dimensional frame of reference that guides a stereotactic procedure. In some instances, the three dimensional coordinate system can be a Cartesian coordinate system. In other instances, the three dimensional coordinate system can be a polar coordinate system. For example, the patient's brain can be depicted in one or more cross sections, each in reference to a two coordinate frame, so that each cross section can be assigned a range of three coordinate numbers that can be used for positioning a stereotactic device.

As used herein, the term "coordinate numbers" or "coordinates" can refer to three dimensions in the three dimensional coordinate system that can be used to identify a target area. For example, in a Cartesian coordinate system, the coordinates can include an x-value that corresponds to a latero-lateral dimension, a y-value that corresponds to a dorso-ventral dimension, and a z-value that corresponds to a rostero-caudal dimension. As another example, in a polar coordinate system, the coordinates can include an angle coordinate, a depth coordinate, and an anterio-posterior location coordinate.

As used herein, the term "target area" can refer to a selection from the identified one or more points that correspond to an anatomical location (e.g., inside the brain). The target area can be identified and/or localized with coordinates within the three-dimensional coordinate system. For example, a medical instrument can be implanted to the target area in a stereotactic procedure.

As used herein, the terms "medical instrument", "instrument", "medical device", "device", and "surgical instrument" can refer to a device that is implanted within the target area during a stereotactic procedure. Examples of the medical instrument can include one or more of: a recording electrode, a stimulating electrode, a biopsy instrument, a catheter, a delivery device, or the like.

As used herein, the term "stereotactic device" can refer to a mechanical apparatus that can fix or hold a patient's head in a position in reference to the coordinate system to enable implantation of the medical instrument into the target area. For example, the stereotactic device can include a body, a guide, and an implantation device to facilitate the implantation of the medical instrument into the target area and can attach to a frame that fixes the patient's head in the position in reference to the coordinate system.

As used herein, the term "orthogonal" can pertain to or involve axes that are perpendicular to each other.

As used herein, the term "implantation" can refer to an act performed using the stereotactic device to place a medical instrument at a target area. Unless noted otherwise, the terms "implantation" and "placement" can be used interchangeably herein.

As used herein, the term "u-shaped" can refer to a shape with at least two connected sides. One example of a u-shaped device can have two sides connected at one end (e.g., a v-shape). As another example, the u-shaped device can have at least three sides connected at two or more places (e.g., two vertical sides and one horizontal side, two horizontal sides and one vertical side, or the like).

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to stereotactic surgery, a minimally invasive form of surgical intervention that makes use of a three dimensional coordinate system to locate a target area within a patient's body so that an action can be performed on the target areas. In some instances, the action can involve implanting a medical instrument (e.g., a recording electrode, a stimulating electrode, a biopsy instrument, a catheter, a drug delivery device, or the like) into the target area. More specifically, the present disclosure relates to systems and methods that can employ a stereotactic device, which aids in the safe, precise placement of the medical instrument in the target area, for the stereotactic surgery. The stereotactic device can have a simple, compact, cost-effective design, while still providing safe, precise placement of multiple medical instruments within multiple target areas. The stereotactic device also can allow for multiple precise and different angle trajectories in a short period of time without the need to reposition the stereotactic frame, adjust the coordinate system, or re-prep/re-drape the patient.

III. Systems

One aspect of the present disclosure can include a stereotactic implantation system 10, as shown in FIG. 1. The system 10 can facilitate simplified and precise orthogonal implantation of medical instruments into target areas within a patient's body without changing coordinate systems or breaking sterility. The system 10 can include a frame 12 and a stereotactic device 14. In some instances, the frame 12 can be a standard stereotactic frame distinct from the stereotactic device 14. However, in other instances, the frame 12 can be embodied within the stereotactic device 14, where at least a portion of the stereotactic device 14 acts a the frame 12.

The system 10 can include the frame 12, which can be attachable to a portion of a patient's body. In some instances, the portion of the patient's body to the patient's head (e.g., using one or more skull bones as anchors). The system 10 can also include the stereotactic device 14 that can facilitate a precise stereotactic implantation of one or more medical instruments within the portion of the patient's body. For example, the stereotactic device 14 can attach to the frame 12, which is attached to the patient's body, to provide stability for the implantation of the medical instruments. The medical instruments can include, for example, one or more recording electrodes, one or more stimulating electrodes, one or more biopsy instruments, one or more catheters, one or more drug delivery devices, or the like. At least a portion of the stereotactic device can ensure that each of the one or more medical instruments is implanted within a specific target area of the patient's body. For example, the target area of the patient's body can be located at a position within the brain required for a stereotactic neurosurgery application. Indeed, the stereotactic device 14 can be used to implant a plurality of medical instruments into a plurality of target areas (at different locations) within the patient's brain using a single coordinate system. Accordingly, the stereotactic device 14 is not required to be removed and reset during the surgical procedure and, thus, does not require a break in sterility for the patient.

The stereotactic device 14 can include a body 16 that can provide a stable, fixed frame of reference for the stereotactic device 14 during implantation of one or more medical device into one or more target areas within the patient's body. In some instances, the stability of the body 16 is accomplished once attached to the frame 12, which can be previously attached to the patient. However, in other instances, the body 16 can directly attach to the patient without the need for the frame 12 (e.g., the body can act as a frame). The body 16 can be sized and dimensioned to be larger than the size of the portion of the patient's body to which the body 16 will be attached. For example, when the portion of the patient's body is the patient's head, the body 16 can be sized and dimensioned to be at least larger than the patient's head. In some instances, the body 16 can have one or more "adult" sizes to correspond to different sized bodies. However, in these instances, the body 16 can have an adjustable size so that a certain size body 16 can be adjusted to accommodate different sized patients. In other instances, the body 16 can have a "pediatric" size which can be smaller than an adult size. The size and/or shape of the body 16 can facilitate the implantation of medical instruments into the target areas at multiple lateral trajectories (including different angles and coordinates) in a short period of time without the need to re-position the frame or re-drape the patient.

Figure 2:
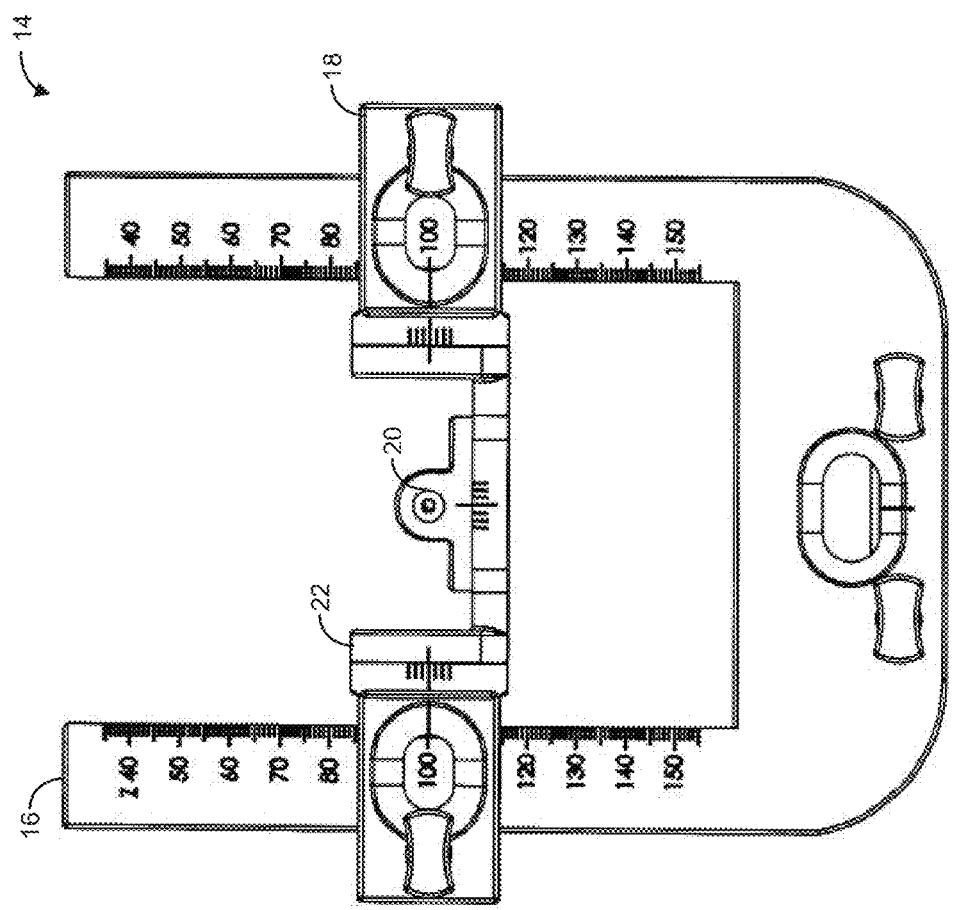
FIG. 2 is a front view of an example stereotactic device, which can be used in the system of FIG. 1.
Figure 3:
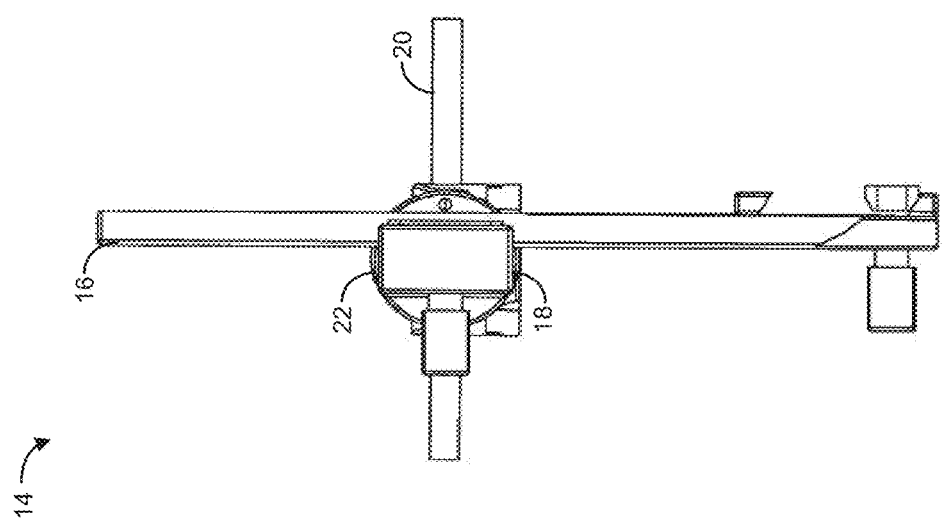
FIG. 3 is a side view of the example stereotactic device shown in FIG. 2.
Figure 4:
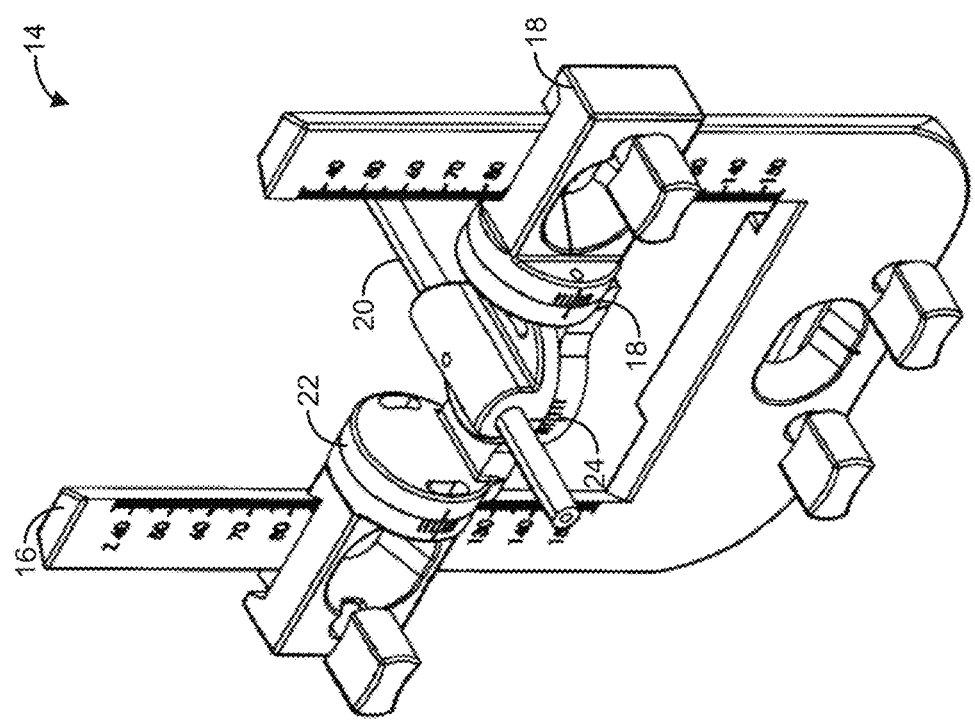
FIG. 4 is an isometric view of the example stereotactic device shown in FIG. 2.

In some instances, the body 16 can include at least two sides separated by a distance greater than a width of a patient's head. In some instances, as shown in the examples of FIGS. 2-4, the body 16 can have a u-shape with two sides and a center portion connecting the two sides. For example, the u-shape can be sized and dimensioned to fit around the patient's head. In other instances, however, the body 16 need only include one side (e.g., half of the u-shape). In the u-shape example, the center portion of the body 16 can include one or more holes and/or one or more attachment mechanisms that can be used to affix the body 16 to the frame 12 and/or the patient's body (e.g., the head).

Once affixed to the frame 12 and/or the patient's body, the body 16 can provide a stable base for motion of other portions of the stereotactic device 14, such as a guide 18. The guide 18 can control the location for the precise implantation of the one or more medical instruments into the target area of the patient's brains along different trajectories. Accordingly, the guide 18 can be moveable with respect to the body 16 and lockable in various positions to facilitate the implantation of the one or more medical devices. Accordingly, the guide 18 can include locking mechanisms that can lock the instrument holder 20 into place for an implantation and unlock to facilitate movement of the instrument holder 20 to new locations for other implantations.

As shown in FIGS. 2-4, the guide 18 can extend between two sides of the body so that the guide 18 is moveable along the length of the two sides of the body 16 and lockable above the target area within the patient's body. For example, the guide 18 can move along the sides of the body 16 to provide motion in the z-direction. As shown in FIGS. 2-4, the body 16 can have markers (or a ruler) on one or more of the sides of the u-shape for coarse adjustment of the position of the guide 18. The mechanism for fine adjustment in the z-direction can be provided by markings near the hole of the guide 18. The mechanism for fine adjustment in the z-direction can be located on the guide 18 perpendicular to the sides of the u-shaped body 16. As shown, the fine adjustment mechanism can include one or more rotational motion mechanisms 22 (e.g., disk-shaped mechanisms).

The guide 18 can be moveable to different positions along the body 16 so that multiple medical instruments can be implanted at multiple lateral trajectories. In some instances, the guide 18 can be rotatable (e.g., rotational motion mechanism 22). The guide 18 can be fixed at different locations to facilitate implantation of the different medical instruments. In some instances, the implantation can be aided by an instrument holder 20, which can be affixed to the guide 18. In some instances, the instrument holder 20 can be affixed to the middle of the guide 18. The instrument holder 20 in combination with the guide 18 can facilitate the implantation of the medical instrument into the target area within the patient's body.

The injection of the medical instrument can be along a predefined trajectory that is defined by the guide 18 and the instrument holder 20. The guide 18 can allow the instrument holder 20 to move in a controlled manner in different directions to provide for many medical instruments to be implanted into many target areas in a short period of time. For example, the guide 18 can move the instrument holder 20 in a linear fashion and/or a rotational fashion (e.g., rotational motion mechanism 22) in at least two directions. Once the instrument holder 20 is positioned in a desired position above the target area, the guide 18 can lock into place to for the implantation of the medical instrument into the target area. The medical instrument can be implanted to the target area through the instrument holder 20. In fact, by permitting linear and rotational motion of the instrument holder 20, the stereotactic device can allow the implantation of a plurality of medical instruments into a plurality of targets areas using a single coordinate system.

As another example (shown in FIGS. 8 A and B), the guide 18, the body 16, and the instrument holder 20 can be part of a bulls-eye lateral implantation system (BLIS). The BLIS can include two rings that can attach to a lateral bar of a stereotactic device 14, such as that shown in FIGS. 2-4 or another commercially available stereotactic device (e.g., a Leksell frame, a CRW frame, or the like). The BLIS can facilitate implantation of one or more medical instruments in an orthogonal orientation in relation to the stereotactic device 14. In some instances, the BLIS can include two rings, a fixation screw, and adaptable reducing tubes. The two rings can be fixed to the stereotactic device 14 by a fixation screw that allows stability and precision. The BLIS can also be connected to a reducing tube system, shaped in various diameters (e.g., any value between 1 mm and 25 mm) allowing for the precise placement of various medical instruments. For example, the medical instruments can include twist drills for burr holes, depth electrodes, or any other device that requires precision in targeting. For example, reducing tube adaptors can be replaceable (e.g., different diameters and lengths), adjusting to any clinical conditions and specific targets. The reducing tubes have a variable length (e.g., any value between 5 cm and 20 cm), which can allow for the precise penetration of the tube through the BLIS to the patients' skin, serving as an anchoring system, adding stability and precision to the device.

The system 10 can be used to implant medical instruments into a patient's head during many neurosurgical procedures. For example, the stereotactic device can provide a simplified method for precise implantation of orthogonal medical devices into the patient's head, such as the acute implantation of intra-cranial depth electrodes necessary for a for a stereo-electroencephlaography (SEEG) procedure. For example, the SEEG procedure can be used to evaluate intractable epilepsy to provide guidance for surgical planning. With SEEG, the seizure onset zone and areas of spiking can be identified by electrodes in different areas in the patient's head within and around epileptic lesions and areas suspected to be part of the seizure network.

The intra-cranial depth electrodes used with SEEG must be precisely implanted to acute target areas in the brain so that they can record activity at specific sites within the brain. The stereotactic device 14 facilitates this precise implantation of the depth electrodes at the different locations without needing to be moved. The body 16 provides a stable base to allow implantation from one position, eliminating the need for multiple coordinate adjustments and breakage in sterility. The guide 18 accommodates the multiple lateral trajectories (in different angles and coordinates) in a short period of time without the need to re-position the frame or re-drape the patient. The stereotactic device 14 is cost-effective and may replace expensive robotic and frameless base systems. The stereotactic device 14 provides a simple, safe, and cost effective alternative to other methods of implantation of SEEG depth electrodes, such as the Talairach frame, the Leksell frame, a robotic device, or any other traditional stereotactic device.

Upon implantation, the intra-cranial electrodes used in the SEEG procedure must be secured in position in the brain to prevent migration of the electrode (e.g., out of the original trajectory). In some instances, the intra-cranial electrodes can be secured by a fixation device that secures a screw cap to a polymer ring using rotational compression. The polymer ring can be placed at the proximal end of the intra-cranial electrode and the screw cap placed on the bolt. Screwing the screw cap to the polymer ring creates a rotational tightening that fixes the intra-cranial electrode in place. These fixation devices also provide a barrier between the internal and external environments. However, there are several limitations to using these fixation devices. First, the fixation devices extend from the patient's head, which is both uncomfortable to the patient and often limiting to the use of imaging. Additionally, the rotational compression used to secure the intra-cranial electrodes can guide the electrode even slightly off trajectory, which can lead to erroneous recordings, and even damage the brain tissue.

Alternatively, after implantation, the intra-cranial electrode can be secured in place by inter-fitting lumen of a different fixation device, rather than rotational compression, to provide the mechanical stability necessary for precise insertion of electrodes into the brain. The different fixation device can include four primary polymer components: (1) a primary housing that screws securely into the skill and has an inner lumen diameter that can at least fit the electrode, (2) a securing housing with a tapered lumen that inserts into the primary housing lumen, (3) a screw cap that compresses the securing housing into the primary housing without rotation, and (4) a detachable cannula length that provides stability during electrode insertion. Advantageously, the different fixation device extends a minimal distance from the skin surface, providing more comfort to the patient, as well as greater access to imaging procedures.

IV. Methods

Figure 5:
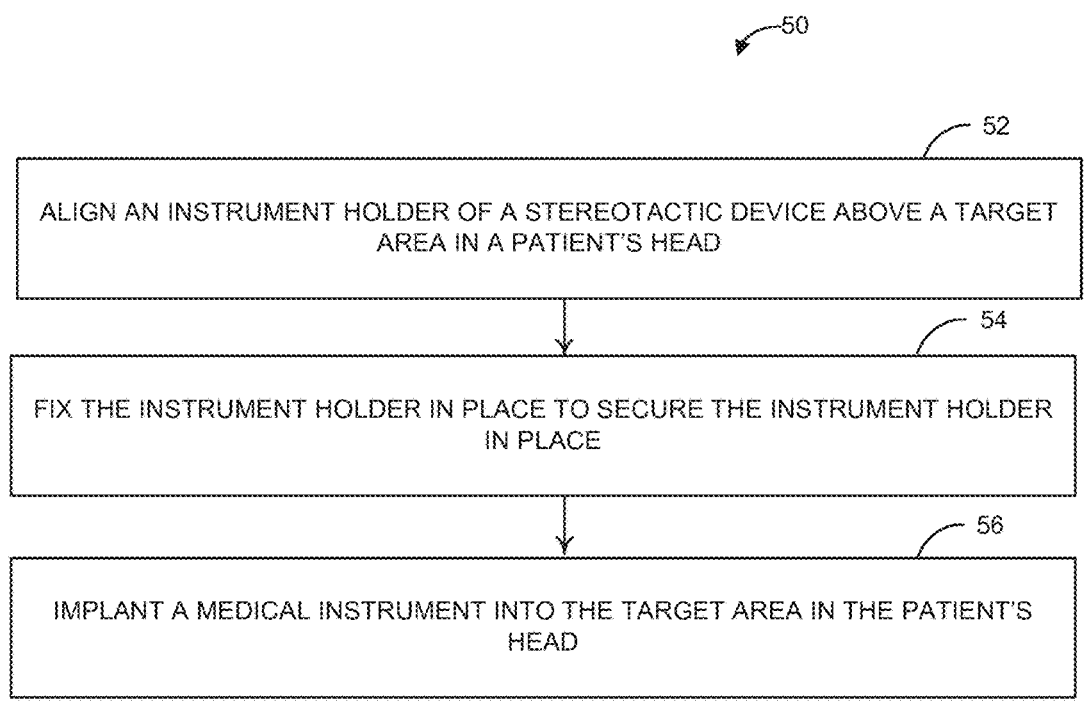
FIGS. 5 and 6 are process flow diagrams illustrating methods for stereotactic implantation in accordance with another aspect of the present disclosure.
Figure 6:
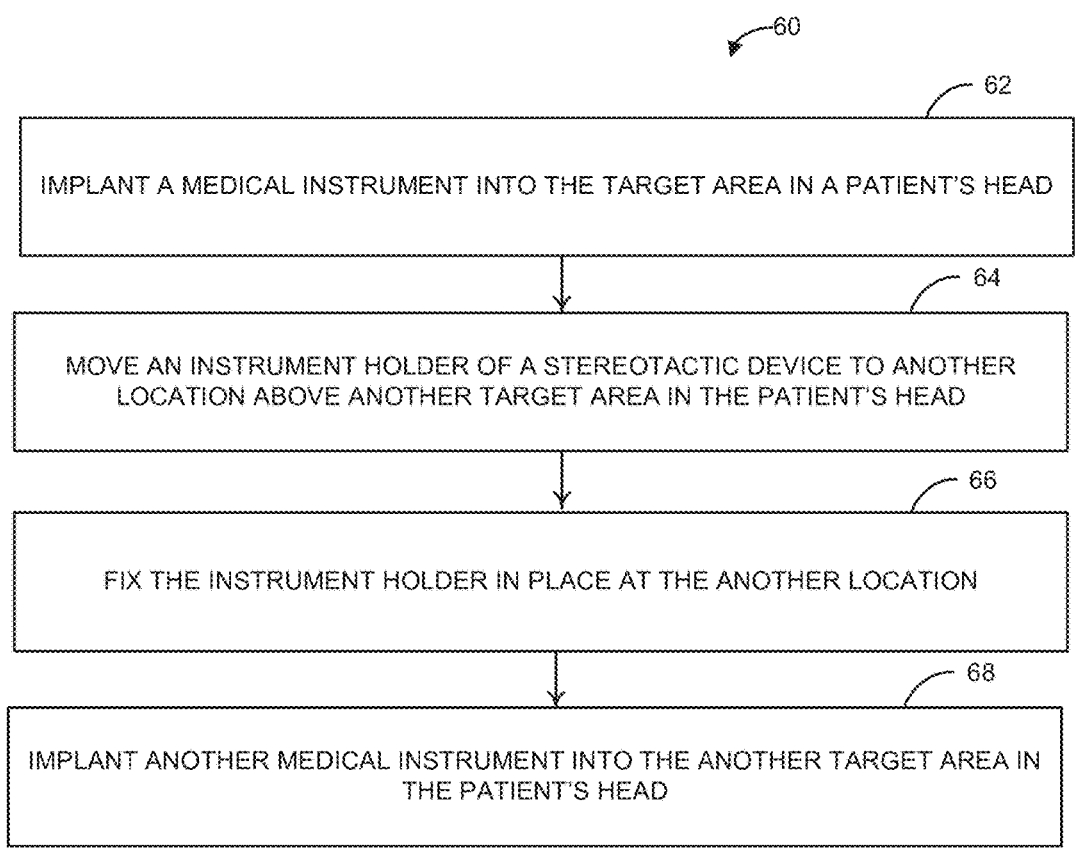

Another aspect of the present disclosure can include methods 50 and 60 for stereotactic implantation as shown in FIGS. 5 and 6. The stereotactic implantation can involve the delivery of one or more medical instrument (e.g., a recording electrode, a stimulating electrode, a biopsy instrument, a catheter, a drug delivery device, and the like) to one or more target area within a patient's body (e.g., the patient's brain) during a stereotactic procedure. The methods 50 and 60 can be accomplished using the stereotactic implantation system 10, as shown in FIG. 1. A method 70 is shown for the stereotactic implantation of intra-cranial electrodes.

The methods 50-70 are illustrated as process flow diagrams with flowchart illustrations. For purposes of simplicity, the methods 60-80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50-70.

FIG. 5 illustrates a method 50 for stereotactic implantation of a medical device into a target area within a patient's body. Although the target area is located in the brain, as illustrated in FIG. 5, the target area need not be in the brain. The stereotactic implantation can be accomplished using a stereotactic device 14 attached to a frame 12, as shown in FIG. 1. The stereotactic device 14 can facilitate precise orthogonal implantation of different medical devices into different target areas without changing a coordinate system.

At 52, an instrument holder of a stereotactic device can be aligned above a target area in a patient's head. The stereotactic device can include a base that remains fixed, providing stability to the stereotactic device, and a guide portion that is movable for coarse and fine (linear and/or rotational) adjustment of the position of the instrument holder. For example, the stereotactic device (as shown in FIGS. 2-4) can include at least a u-shaped body to secure the stereotactic device to the patient's head, a guide attached between sides of the u-shaped body, and an instrument holder attached to the guide to receive medical instruments for implantation into the target area of the patient's brain. At least a portion of the guide can be moveable to implant the medical instrument into different target areas and fixable in position for the implantation. At 54, the instrument holder can be fixed in place above the target area. At 56, a medical instrument can be implanted into the target area in the patient's head through the instrument holder and the guide For example, the medical instrument can be a recording electrode, a stimulating electrode, a biopsy instrument, a catheter, a drug delivery device, or the like. The instrument holder can be unlocked and moved to another location for the implantation of other instruments.

FIG. 6 illustrates a method 60 for stereotactic implantation that is a continuation of the method 50 of FIG. 5. At 62 (similar to 66) a medical instrument can be implanted into a target area in the patient's head (e.g., through the instrument holder and the guide of the stereotactic device). At 74, the instrument holder of the stereotactic device can be moved to another location above another target area in a patient's head. At 76, the instrument holder can be fixed in place at the another location. At 78, another medical instrument can be implanted into the another target area in the patient's head. For example, the medical instruments can be implanted into two target areas according to different trajectories without requiring a change in the coordinate system.

Figure 7:
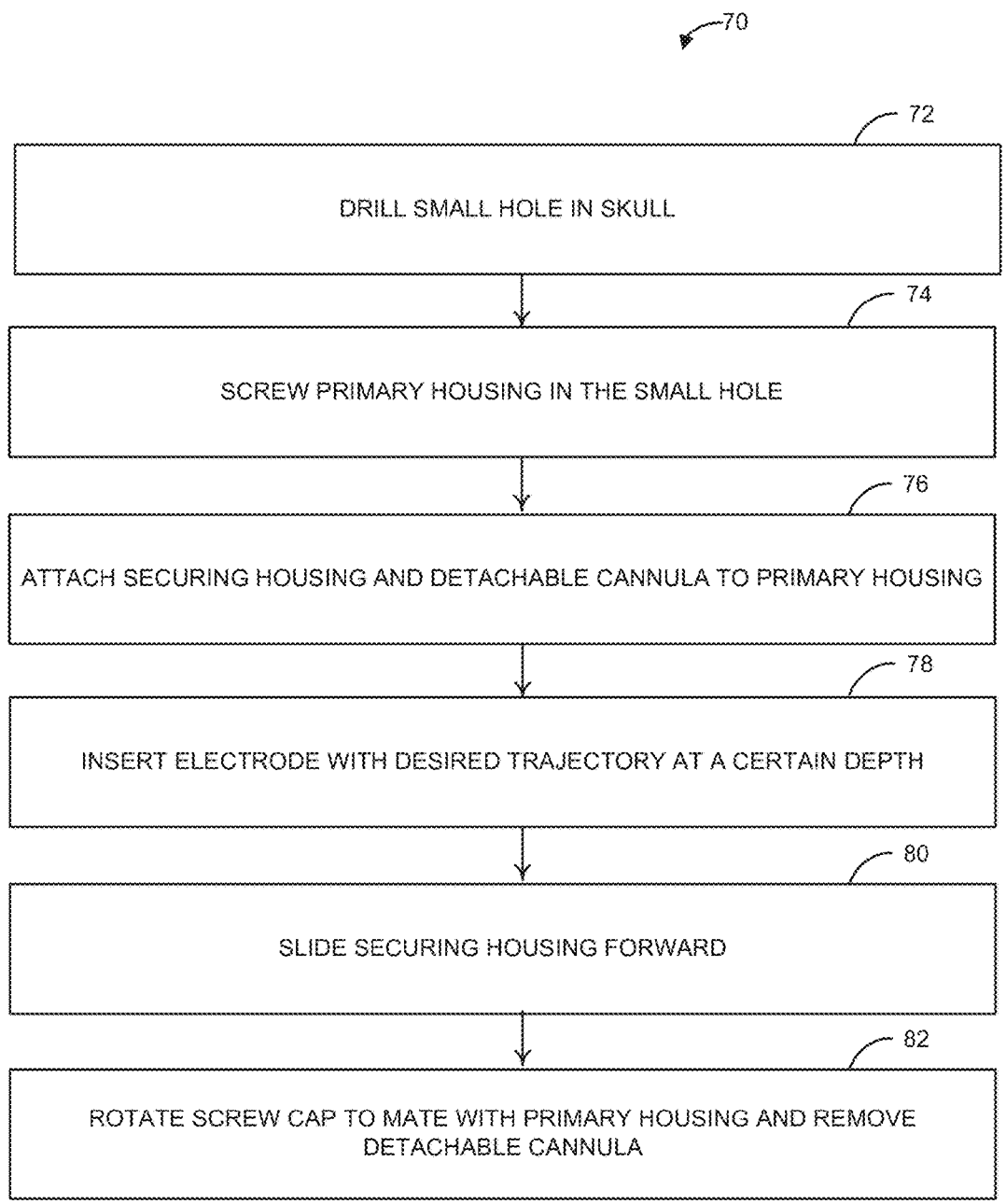
FIG. 7 is a process flow diagram illustrating a method for stereotactic implantation of intra-cranial electrodes, according to another aspect of the present disclosure.

FIG. 7 illustrates a method 70 for the stereotactic implantation of intra-cranial electrodes. The intra-cranial electrodes are an example of medical devices that can be implanted by the system 10 of FIG. 1. The intra-cranial electrodes can be implanted using a fixation device that includes four primary polymer components: (1) a primary housing that screws securely into the skill and has an inner lumen diameter that can at least fit the electrode, (2) a securing housing with a tapered lumen that inserts into the primary housing lumen, (3) a screw cap that compresses the securing housing into the primary housing without rotation, and (4) a detachable cannula length that provides stability during electrode insertion. The electrode can be inserted using the fixation device as follows.

At 72, a small hole is drilled in the skill. For example, the hole can be drilled by a surgeon using a stereotactic device (e.g., stereotactic device 14 as shown in FIG. 1). At 74, the primary housing can screw securely into the small hole in the skull. At 76, the securing housing can be attached to the primary housing with the detachable cannula length to facilitate insertion of the electrode. At 78, the electrode can then be inserted into the brain on a desired trajectory and at a desired depth. Upon insertion of the electrode, at 80, the securing housing can be slid forward. Sliding the securing housing forward projects the tapered lumen of the securing housing into the non-tapered lumen of the primary housing, securing the electrode and providing a water-tight seal. At 82, the screw cap can be rotated, without rotation of the secure housing, to mate with the threaded proximal end of the primary housing and the detachable cannula length can be removed and discarded. When the cannula length is removed, the fixation device only extends a minimal distance from the skin surface, allowing the patient more comfort and access to imaging.

From the above description, those skilled in the art will perceive improvements, changes and modifications. Such improvements, changes and modifications are within the skill of one in the art and are intended to be covered by the appended claims.

What is claimed is:

1. A method comprising:
   fixing a stereotactic device to a frame attached to a patient's head, wherein the stereotactic device comprises:
      a body having a U-shape and comprising two sides separated by a distance; and
      a guide extending from one of the two sides of the body to another of the two sides of the body, wherein the guide is lockable at a position between the two sides and a portion of the guide is rotatable;
   performing a coarse movement of the guide to a position along the two sides,
   wherein the position is above a target area within the patient's head;
   locking the guide at the position;
   performing a fine adjustment of an instrument holder attached to the guide by linear and/or rotational movement;
   locking the instrument holder in place after the fine adjustment;
   implanting a medical instrument to the target area within the patient's head through the instrument holder attached to the guide;
   unlocking the guide;
   performing another coarse movement of the guide to a second position along the two sides, wherein the second position is above a second target area within the patient's head;
   locking the guide at the second position;
   performing another fine adjustment of the instrument holder attached to the guide by linear and/or rotational movement;
   locking the instrument holder in place after the other fine adjustment; and
   implanting a second medical instrument to the second target area within the patient's head through the instrument holder attached to the guide.

2. The method of claim 1, wherein the body remains fixed as the guide is moved to the second location.

3. The method of claim 1, wherein the first target area and the second target area are orthogonal to each other.

4. The method of claim 1, wherein the implantations of the medical instruments to the target areas are achieved according to different lateral trajectories.

5. The method of claim 1, wherein the medical instrument is at least one of a recording electrode, a stimulating electrode, a biopsy instrument, a catheter, and a drug delivery device.

* * * * *